United States Patent [19]

Nappa

[11] Patent Number: 5,091,168
[45] Date of Patent: Feb. 25, 1992

[54] PREPARATION OF ANHYDROUS NIOBIUM AND TANTALUM PENTAFLUORIDES

[75] Inventor: Mario J. Nappa, Newark, Del.

[73] Assignee: E. I. Du Pont de Nemours and Company, Wilmington, Del.

[21] Appl. No.: 567,815

[22] Filed: Aug. 15, 1990

[51] Int. Cl.$^5$ .............................................. C01G 35/02
[52] U.S. Cl. .................................... 423/489; 423/492
[58] Field of Search ................................ 423/489, 492

[56] References Cited

U.S. PATENT DOCUMENTS

| | | | |
|---|---|---|---|
| 4,065,405 | 12/1977 | Hulme | 423/492 |
| 4,069,268 | 1/1978 | Siskin et al. | 423/492 |
| 4,098,833 | 7/1978 | Wristers | 502/22 |
| 4,120,912 | 10/1978 | Hulme | 585/374 |
| 4,124,692 | 11/1978 | Kim et al. | 423/492 |
| 4,469,804 | 9/1984 | Johnson | 502/32 |
| 4,678,769 | 7/1987 | King | 502/231 |
| 4,752,454 | 6/1988 | Pastor et al. | 423/489 |

*Primary Examiner*—John Niebling
*Assistant Examiner*—Brian M. Bolam
*Attorney, Agent, or Firm*—Robert B. Stevenson; Michael K. Boyer

[57] ABSTRACT

A method of producing an anhydrous niobium or tantalum pentafluoride involving reacting the corresponding pentoxide or oxyhalide with an excess of anhydrous hydrogen fluoride in the presence of a sufficient dehydrating agent (e.g., $COCl_2$, $SOCl_2$ or $SO_2Cl_2$) to react with any water formed. Such a process is useful to produce a catalyticallyactive anhydrous niobium or tantalum pentafluoride in essentially a single liquid phase reaction step.

12 Claims, No Drawings

PREPARATION OF ANHYDROUS NIOBIUM AND TANTALUM PENTAFLUORIDES

BACKGROUND OF THE INVENTION

1. Field of the Invention

This invention relates to a process for the preparation of anhydrous niobium and tantalum pentafluorides. More specifically, the invention relates to reacting a niobium or tantalum pentoxide with an excess of anhydrous hydrogen fluoride in the presence of a dehydrating agent such as to produce catalytically active anhydrous niobium or tantalum pentafluoride.

2. Description of the Related Art Including Information Disclosed Under 37 CFR §§1.97-1.99

It is generally known that tantalum pentafluoride ($TaF_5$) and niobium pentafluoride ($NbF_5$) are useful in the petroleum processing industry as isomerization and alkylation catalysts. Tantalum pentafluoride and niobium pentafluoride are also useful as fluorination catalysts in the preparation of chlorofluorinated hydrocarbons by catalyzing the addition of hydrogen fluoride or by catalyzing the exchange reaction of fluorine for chlorine in chlorocarbons or chlorohalocarbons.

Various methods of preparing tantalum and niobium pentafluorides have been proposed. Typically they are prepared by passing fluorine gas over niobium or tantalum metals or chlorides at elevated temperatures; however, the high costs associated with the production of niobium and tantalum metals and the expensive use of elemental fluorine with the special equipment required to compensate for the corrosive and reactive nature of the gas make niobium and tantalum pentafluorides prepared by this method very expensive. It is also generally known in the prior art that the catalytic activity of tantalum and niobium pentafluoride gradually decline due to the accumulation of various contaminants or poisons and in particular because of the accumulation of water or other oxygen containing compounds. Thus, there is an incentive to regenerate a spent tantalum or niobium pentafluoride catalyst and various methods of accomplishing this have been proposed.

For example, in a pair of U.S. Pat. Nos., 4,098,833 and 4,120,912, methods of regenerating liquid phase Friedel-Crafts type hydrocarbon conversion catalyst comprising a metal halide (including tantalum and niobium fluoride) used with a Bronsted acid (such as HF) are described. In the first reference, the spent catalyst is contacted with a noble metal and hydrogen at 0° to 150° C. while in the second reference the spent catalyst is contacted with hydrogen at a partial pressure of at least one atmosphere and at a temperature of 100° to 500° C. In U.S. Pat. No. 4,469,804 the regeneration of a niobium or tantalum catalyst chemically bonded to solid support wherein the supported catalyst has been deactivated by contact with oxygen or a compound containing oxygen is disclosed. In this regeneration process the spent solid catalyst and support are contacted with a liquid or gaseous halogenated hydrocarbon at conditions that thermodynamically favor the conversion of niobium or tantalum pentoxide to niobium or tantalum pentahalide.

U.S. Pat. No. 4,124,692 discloses a method of preparing and regenerating anhydrous $TaF_5$ from a mixture of water and fluorotantalic acids using a dehydrating agent. In this reference an aqueous mixture of tantalum oxide and tantalum oxyhalide is first reacted with hydrogen fluoride to produce a mixture of water and fluorotantalic acids. After removing excess HF, a dehydrating agent, such as phosgene or chloroform, is then added to react with the water. According to this prior art reference, the dehydration reaction is effective when the ratio of oxygen to tantalum is about 1.5 or less and when an oxygen to tantalum ratio of 2 or more is present and the temperature is about 100° C. the mixture of water and fluorotantalic acids decomposes to form an oxyfluoride and HF, thus representing conditions at which the dehydration reaction will not proceed satisfactorily. In the case of a mixture of water and fluorotantalic acids formed from the reaction of tantalum pentoxide, $Ta_2O_5$, and HF the oxygen to tantalum ratio is inherently 2.5. Therefore, the prior art reference teaches that the ratio must be adjusted downward, preferably to 1.25, by the addition of 2 moles of anhydrous $TaF_5$ for every mole of $Ta_2O_5$ starting material. This addition of anhydrous $TaF_5$ must be done before the addition of a dehydrating agent, consequently this prior art process is essentially a three-step or stage process.

SUMMARY OF THE INVENTION

In view of the prior art and, in particular, the need for an inexpensive and reliable method of preparing anhydrous niobium and tantalum pentafluorides and/or regenerating spent niobium tantalum pentafluoride catalyst, the present invention provides an essentially single stage or one-step process for preparing and/or regenerating both niobium and tantalum pentafluorides. According to this process, the oxides, oxyhalides or mixtures of oxide and oxyhalides of pentavalent tantalum or pentavalent niobium are contacted with an excess of anhydrous hydrogen fluoride in the presence of an effective amount of a dehydrating agent such as to react any water produced. Preferably the dehydrating agent is phosgene such that the gaseous reaction products associated with the dehydrating reaction readily separate from the liquid phase HF, thus producing the desired anhydrous tantalum or niobium pentafluoride in a media amenable for use in a hydrodechlorination reaction. It has been further discovered that the presence of residual phosgene is not detrimental to the subsequent hydrodechlorination reactions. The process according to the present invention is particularly useful for preparing anhydrous niobium or tantalum pentafluoride starting from the corresponding oxide or regenerating a spent niobium or tantalum pentafluoride catalyst that has been deactivated by water or other oxygen-containing compounds.

Thus, the present invention provides a process for the preparation of an anhydrous niobium or tantalum pentafluoride comprising the steps of:

(a) contacting niobium or tantalum pentoxide or oxyhalide in the presence of an excess of hydrogen fluoride at about 50° C. to about 200° C. for sufficient time to convert at least some of the niobium or tantalum pentoxide or oxyhalide to niobium or tantalum pentafluoride wherein the contacting is in the presence of an effective amount of a dehydrating agent to react with any water formed; and (b) recovering anhydrous niobium or tantalum pentafluoride.

In one specific embodiment, the dehydrating agent is selected from the group consisting of phosgene, thionyl chloride and sulfuryl chloride. In another embodiment, the excess hydrogen fluoride is present with at least 10 moles of hydrogen fluoride per mole of niobium or tantalum pentoxide.

It is an object of the present invention to provide an inexpensive yet reliable method of preparing anhydrous niobium or tantalum pentafluorides directly from niobium or tantalum pentoxides in essentially one step. It is a further object of the present invention to provide an inexpensive yet reliable method of regenerating the catalytic activity of a niobium or tantalum pentafluoride catalyst that has experienced a decrease in activity by exposure to water or other oxygen-containing compounds. It is an associated object to accomplish the above objects by contacting either tantalum or niobium pentoxides or oxyhalides with HF in the presence of a dehydrating agent. Fulfillment of these objects and the presence and fulfillment of other objects will be apparent upon complete reading of the specification and attached claims.

DETAILED DESCRIPTION OF THE INVENTION

The use of niobium or tantalum pentafluoride as catalysts in hydrocarbon processing industries and in the preparation of chlorofluorinated hydrocarbons require that they be essentially anhydrous. Presence of water or some oxygenated compounds will destroy or greatly diminish the catalytic activities of these pentafluorides. Thus, for purposes of the present invention, the phrases "anhydrous" niobium pentafluoride or "anhydrous" tantalum pentafluoride broadly refer to any catalytically niobium or tantalum pentafluoride.

Niobium or tantalum pentoxide can be treated with hydrogen fluoride to form hydrated pentafluorides as generally illustrated by the following equation (1), using $Ta_2O_5$;

$$Ta_2O_5 + 10HF \rightarrow 5H_2O \cdot 2TaF_5 \quad (1)$$

However, it is difficult to obtain anhydrous $TaF_5$ from the above hydrate. If attempts were made to obtain the anhydrous pentafluorides for example by heating, the product obtained is not anhydrous pentafluoride but an oxyhalide according to equation (2).

$$5H_2O \cdot 2TaF_5 \rightarrow 2TaOF_3 + 3H_2O + 4HF \quad (2)$$

Kim in U.S. Pat. No. 4,124,692 discloses a process for preparing anhydrous TaF5 from a mixture comprising of water and fluorotantalic acids by contacting said mixture with a dehydrating agent. The mixture of water and fluorotantalic acids being originally prepared by contacting tantalum pentoxide or oxyhalide with hydrogen fluoride as represented by the reaction with tantalum pentoxide according to equation (3).

$$Ta_2O_5 + 12HF \rightarrow 5H_2O \cdot 2HTaF_6 \quad (3)$$

An important limitation of Kim's process is that the product of equation (3) cannot be converted to anhydrous TaF5 by the use of a dehydrating agent. Kim teaches (at column 3 lines 11-29) that when the molar ratio of water to fluorotantalic acid is greater than about 1.5, the dehydration reaction with the disclosed dehydrating agents will not proceed to form anhydrous pentafluoride but an oxyfluoride is formed. Kim also teaches (column 3 lines 31-39) that in the mixture obtained in equation (3) wherein the molar ratio of water to fluorotantalic acid is 2.5 (as in product of equation (1)), anhydrous TaF5 can be obtained only if to such a mixture extraneous anhydrous TaF5 is first added to reduce the molar ratio of water to fluorotantalic acid to 1.25 or less. Kim's examples 1 and 2 clearly illustrate this necessity of adding extraneous anhydrous TaF5 to a mixture of water and fluorotantalic acid obtained by treating $Ta_2O_5$ with hydrogen fluoride to obtain anhydrous TaF5. Thus, the major disadvantage of Kim's process for preparing anhydrous TaF5 from $Ta_2O_5$ is that at least an equivalent amount extraneous anhydrous TaF5 must be added during the process for the process to be practical.

It has now been discovered that anhydrous niobium pentafluoride or anhydrous tantalum pentafluoride can be prepared from niobium pentoxide or tantalum pentoxide, the process not requiring the required use extraneous anhydrous pentafluorides as taught by Kim. The present process comprises heating niobium pentoxide or tantalum pentoxide with a mixture of hydrogen fluoride and a dehydrating agent such as phosgene, thionyl chloride or sulfuryl chloride in the temperature range of from about 50° C. to about 200° C.

The amount of hydrogen fluoride to be used with niobium pentoxide or tantalum pentoxide in the present process should be at least ten moles of hydrogen fluoride per mole of the pentoxide according to equation (1) to form the pentafluorides. Generally, somewhat more than the stoichiometric amount of hydrogen fluoride is used to maximize the use of the pentoxides and to facilitate the reaction. Thus, the amount of hydrogen fluoride used can be from the stoichiometric amount of 5 moles of hydrogen fluoride per mole of niobium or tantalum pentoxide to about 50 moles of hydrogen fluoride per mole of the metal oxides. If desired, even greater amounts of hydrogen fluoride can be used without deviating from the scope of the present invention. Preferably, the hydrogen fluoride used is anhydrous hydrogen fluoride but technical hydrogen fluoride containing up to about 5% water can be used.

While a number of dehydrating agents such as sulfuryl chloride ($SO_2Cl_2$), thionyl chloride ($SOCl_2$) and the like can be used, the particularly preferred dehydrating agent of the present invention is phosgene ($COCl_2$) which is used together with hydrogen fluoride to convert niobium pentoxide or tantalum pentoxide to respective anhydrous pentafluorides. The stoichiometry of the reaction as indicated by equation (1) calls for five moles of phosgene (i.e., dehydrating agent) to react with five moles of water generated in the reaction. Thus, there should be at least five moles of phosgene per mole of the metal oxide used. Generally, it is preferred to use excess phosgene in the range of from about 6 to about 30 moles of phosgene per mole of the metal oxide used. Use of even greater amounts of phosgene is not harmful and is within the scope of the present invention.

The temperature for the reaction of niobium pentoxide or tantalum pentoxide with hydrogen fluoride and phosgene is in the range of from about 50° C. to about 200° C., preferably in the range of from about 75° C. to about 160° C. The pressure at which the reaction is carried out is not critical and is preferably the autogenous pressure developed by the reactants and the products at the reaction temperature in a closed reactor. In general, the autogenous pressure will be in the range of from about 100 psi to about 1000 psi when the reaction temperature is as described above and excess hydrogen fluoride and phosgene are added to either niobium pentoxide or to tantalum pentoxide in an equipment suitable for use with hydrogen fluoride. The mixture is heated to the temperature range of from about 50° C. to about 200° C., preferably to the range of from about 75° C. to about 160° C., allowing autogenous pressure to develop. The reaction time is from about one hour to about ten hours, but generally the reaction is complete in about three to about five hours in the preferred temperature range. The volatile products are then removed e.g. by distillation at reduced pressures leaving behind either anhydrous niobium pentafluoride or anhydrous tantalum pentafluoride. That the products obtained are anhydrous niobium pentafluoride or anhydrous tantalum pentafluoride can be confirmed by elemental analyses. Another practical confirmation is in using the products obtained as catalysts in the fluorination reactions. Thus, it is known, for example, that only anhydrous tantalum pentafluoride will catalyze the reaction between tetrachloroethylene and hydrogen fluoride to produce various chlorofluorinated ethanes. Tantalum oxyfluoride does not catalyze such a reaction.

As shown in the examples, anhydrous pentafluorides produced by the process of the present invention are effective catalysts in the fluorination reactions. In the examples, perclene (tetrachloroethylene) was reacted with hydrogen fluoride in the presence of anhydrous tantalum pentafluoride prepared according to the process of the present invention to produce chlorofluorinated ethanes including 1,1-dichloro-2,2,2-trifluoroethane, 1,1,2,2-tetrachloro-2-fluoroethane and 1,1,2-trichloro-2,2-difluoroethane.

The unexpected advantages of the present process over prior art process of Kim U.S. Pat. No. 4,123,692 for the preparation of anhydrous tantalum pentafluoride are related to the following differences:

Kim's teachings for the preparation of anhydrous $TaF_5$ from $Ta_2O_5$ require the steps of (a) reacting $Ta_2O_5$ with excess hydrogen fluoride, (b) removing the excess hydrogen fluoride, (c) adding anhydrous $TaF_5$ to reduce the water to fluorotantalic acid ratio to 1.5 or less for the ratio of 2.5 obtained in steps (a) and (b), (d) adding dehydrating agent to remove water and (e) removing excess dehydrating agent to remove anhydrous tantalum pentafluoride.

In contrast thereto, the present process for the preparation of anhydrous $TaF_5$ from $Ta_2O_5$ require only the steps of (a) reacting $Ta_2O_5$ with hydrogen fluoride and phosgene followed by (b) removing excess hydrogen fluoride and the volatile products.

Therefore, not only are the number of required steps greatly reduced in the present process, but also very importantly, the present process does not require a supply of anhydrous $TaF_5$ in order to prepare anhydrous $TaF_5$ from $Ta_2O_5$.

The following examples are presented to further illustrate specific embodiments of the present invention for the preparation of anhydrous $NbF_6$ from $Nb_2O_5$ (Examples 1 and 2) and the preparation of anhydrous $TaF_5$ from $Ta_2O_5$ (Examples 3 and 4) and then compare these to the results of the prior art method (Comparative Example 1).

EXAMPLE 1

To a 150 cc stainless steel single ended cylinder in a drybox was added $Nb_2O_5$ (16.1 gm, 60.2 mmol), HF (39.6 gm, 1,980 mmol), $COCl_2$ (27.3 gm, 276 mmol) and a stir bar. The cylinder was then fitted with a reflux condenser operating at 9° C., a pressure gauge and a back pressure regulator set at 500 psi. The cylinder containing the reactants was immersed in an oil bath set at 125°-163° C. and the reaction temperature, monitored by a thermocouple inside of the cylinder, was raised from 93° to 148° C. over a 51 minute period while generating an autogenous pressure increasing from approximately 225 to 505 psi. The temperature of the bath was maintained at 162°-7° C. and the internal temperature varied from 147°-152° C. over 4.9 hours. The reaction pressure remained at 490-505 psi. Excess HF and $COCl_2$ were removed by vacuum transfer, and a dry solid collected (21.2 gm, 113 mmol, 94% yield). $NbF_5$ (calc): Nb, 49.4%; F, 50.6%; (anal) Nb, 48.5; F, 50.0. Calc F:Nb = 5:1.

EXAMPLE 2

To a 150 cc stainless steel, single ended cylinder in a drybox was added $Nb_2O_5$ (14.7 gm, 55.5 mmol), HF (60.3 gm, 3,015 mmol), $COCl_2$ (41.6 gm, 420 mmol) and a stir bar. The cylinder was then fitted with a reflux condenser operating at 9° C., a pressure gauge and a back pressure regulator set at 500 psi. The cylinder containing the reactants was immersed in an oil bath set at 100°-168° C., and the reaction temperature, monitored by a thermocouple inside of the cylinder, was raised from 66° to 148° C. over 53 minutes while generating an autogenous pressure increasing from approximately 115 to 510 psi. The temperature of the bath was maintained at 152°-168 C. and the internal temperature varied from 148°-154° C. over 6.1 hours. The reaction pressure remained at 460-510 psi. Excess HF and $COCl_2$ was removed by vacuum transfer, and a dry solid collected (19.0 gm, 71.5 mmol, 92% yield). $NbF_5$ (calc): Nb, 49.4%; F, 50.6%; (anal) Nb, 48.5; F, 51.3. Calc F:Nb = 5.2.

EXAMPLE 3

To a 150 cc stainless steel single ended cylinder in a drybox was added $Ta_2O_5$ (17.8 gm, 40.3 mmol), HF (40.4 gm, 2,020 mmol), $COCl_2$ (27.2 gm, 275 mmol) and a stir bar. The cylinder was then fitted with a reflux condenser operating at 9° C., a pressure gauge and a back pressure regulator set at 500 psi. The cylinder containing the reactants was immersed in an oil bath set at 125°-165° C., and the reaction temperature, monitored by a thermocouple inside of the cylinder, was raised from 71° to 154° C. over 94 minutes while generating an autogenous pressure increasing from approximately 150 to 510 psi. The temperature of the bath was maintained at 164°-166° C. and the internal temperature was maintained at 154° C. over 3.3 hours. The reaction pressure remained at 510 psi. Excess HF and $COCl_2$ was removed by vacuum transfer, and a dry solid collected (17.8 gm , 64.5 mmol, 80% yield). $TaF_5$ (calc): Ta, 65.6%; F, 34.4%; (anal) Ta, 68.3 ; F, 35.5. Calc F:Ta ratio = 5.0.

EXAMPLE 4

To a 150 cc stainless steel single ended cylinder in a dry box was added $Ta_2O_5$ (13.4 gm, 30.3 mmol) and a stir bar. Hydrogen fluoride (20.4 gm, 1650 mmol) and phosgene (23.0 gm, 233 mmol) were added by vacuum distillation. The cylinder was then fitted with a reflux condenser operating at 9° C., a pressure gauge and a back pressure regulator set at 500 psi. The cylinder was then immersed in an oil bath at 155° C. and the reaction temperature monitored by a thermocouple inside the cylinder was raised from 54° C. to 152° C. over an hour and maintained at 152° C. for 3.8 hours. Autogenous pressure in excess of 500 psi was generated. The cylinder was taken out of the oil bath and cooled. The volatile products were removed by vacuum distillation. In the dry box, perclene (29.8 gm, 180 mmol) and HF (29.0 gm, 1450 mmol) were added to the stainless steel cylinder. The reaction cylinder was reconnected to the reaction system described above and immersed in an oil bath at 99°–157° C., the reaction temperature was raised to 143° C. over 1.3 hours. The reaction temperature was maintained at 138°–143° C. for 2 hours. After cooling the reaction cylinder, the organic products were isolated by vacuum transfer of the contents to a transfer cylinder containing a dip leg. The contents of the transfer cylinder were then blowcased onto ice using nitrogen gas. 23.6 gm of organic products was isolated and analyzed as follows: $CHCl_2CClF_2$ (14.5%) and $CHCl_2CF_3$ (84.4%).

COMPARATIVE EXAMPLE 1

This comparative example demonstrates that when $Ta_2O_5$ is treated according to the teaching found in U.S. Pat. No. 4,124,692, (i.e., of treating $Ta_2O_5$ first with hydrogen fluoride, removing excess hydrogen fluoride, and then treating with dehydrating agent without the benefits of additional anhydrous $TaF_5$). The product obtained is not anhydrous $TaF_5$ and the product does not catalyze the fluorination reaction of perclene with hydrogen fluoride as in Example 3, above.

To a 150 cc stainless steel single ended cylinder in a drybox was added $Ta_2O_5$ (8.76 gm, 19.8 mmol), HF (22.0 gm, 1100 mmol) and a stir bar. The cylinder was then fitted with a reflux condenser operating at 9° C., a pressure gauge and a back pressure regulator set at 500 psi. The cylinder containing the reactants was immersed in an oil bath set at 103°–116° C., and the reaction temperature, monitored by a thermocouple inside of the cylinder was raised from 81° to 113° C. over a 1.2 hour period while generating an autogenous pressure increasing from approximately 85 to 190 psi. At the end of this period, the volatile products were removed by vacuum distillation. Phosgene (9.80 gm, 99.1 mmol) was added to the reaction cylinder, and the cylinder immersed in an oil bath set at 101°–160° C. and the reaction temperature was raised from 39° to 157° C. over 3.8 hours while generating an autogenous pressure increasing from approximately 20 to 415 psi. At the end of this period the volatile products were removed by vacuum distillation. The cylinder was backfilled with nitrogen and capped. In a drybox, perclene (19.5 gm, 118 mmol) was added, and HF (19.6, 980 mmol) were added by vacuum distillation. The reaction cylinder was reconnected to our reaction system (see above) and immersed in an oil bath set at 164° C. for two hours, and the reaction temperature was raised from 148°–153° C. over two hours. Organic products were isolated by vacuum transfer of the contents of the reaction cylinder at the end of the run to a transfer cylinder containing a dip leg. The contents of the transfer cylinder were then blowcased onto ice using nitrogen gas; 9.5 grams of organic were isolated and analyzed as follows: Perclene (97.8%) and $CHCl_2CCl_2F$ (1.7%).

Having thus described and exemplified the invention with a certain degree of particularity, it should be appreciated that the following claims are not to be so limited but are to be afforded a scope commensurate with the wording of each element of the claim and equivalents thereof.

I claim:

1. A process for the preparation of an anhydrous niobium or tantalum pentafluoride comprising the steps of:
   (a) contacting niobium or tantalum pentoxide or oxyhalide in the presence of an excess of hydrogen fluoride at about 50° C. to about 200° C. for sufficient time to convert at least some of said niobium or tantalum pentoxide or oxyhalide to niobium or tantalum pentafluoride wherein said contacting is performed without pentafluoride addition and in the presence of an effective amount of a dehydrating agent to react with any water formed; and
   (b) recovering anhydrous niobium or tantalum pentafluoride.

2. A process of claim 1 wherein said dehydrating agent comprises phosgene.

3. A process of claim 1 wherein said excess hydrogen fluoride is present with at least 10 moles of hydrogen fluoride per mole of niobium or tantalum pentoxide.

4. A process of claim 2 wherein said excess hydrogen fluoride is present with at least 10 moles of hydrogen fluoride per mole of niobium or tantalum pentoxide or oxyhalide.

5. A process of any one of claims 1 or 2 through 4 wherein the temperature is from about 75° C. to about 160° C.

6. A process of any one of claims 1 or 2 through 4 wherein the temperature is about 100° C. through about 200° C.

7. A process for the preparation of an anhydrous niobium or tantalum pentafluoride consisting essentially of:
   (a) contacting niobium or tantalum pentoxide or oxyhalide in the presence of an excess of hydrogen fluoride to convert at least some of said niobium or tantalum pentoxide or oxyhalide to niobium or tantalum pentafluoride wherein said contacting is performed without pentafluoride addition and in the presence of an effective amount of a dehydrating agent to react with any water formed; and
   (b) recovering anhydrous niobium or tantalum pentafluoride.

8. A process for regenerating a catalyst which has been deactivated by an oxygen containing compound comprising the steps of:
   (a) providing a catalyst comprising at least one of niobium and tantalum pentafluorides;
   (b) contacting the catalyst in the presence of an excess of hydrogen fluoride at about 50° C. to about 200° C. for sufficient time to regenerate at least some of said niobium or tantalum pentafluoride wherein said contacting is performed without pentafluoride addition and in the presence of an effective amount of a dehydrating agent to react with any water formed; and
   (c) recovering regenerated anhydrous niobium or tantalum pentafluoride.

9. A process of any one of claims 1, 7 or 8 wherein said dehydrating agent comprises at least one material selected from the group consisting of phosgene, thionyl chloride and sulfuryl chloride.

10. A process of any one of claims 1, 7, or 8, wherein said recovering comprises removing at least one of volatile products and excess hydrogen fluoride.

11. A process of claim 9 wherein said excess hydrogen fluoride is present with at least 10 moles of hydrogen fluoride per mole of niobium or tantalum pentoxide or oxyhalide.

12. A process of claim 1 or claim 7, wherein said recovering comprises recovering catalytically active niobium or tantalum pentafluoride.

* * * * *